United States Patent [19]

Shiokawa et al.

[11] Patent Number: 5,384,324
[45] Date of Patent: Jan. 24, 1995

[54] INSECTICIDALLY ACTIVE CYANO COMPOUNDS

[75] Inventors: Kozo Shiokawa, Kawakasaki; Shinichi Tsuboi, Hino; Koichi Moriya, Tokyo; Ikuro Honda, Tanashi; Yumi Hattori; Katsuhiko Shibuya, both of Hachioji, all of Japan

[73] Assignee: Nihon Bayer Agrochem K.K., Tokyo, Japan

[21] Appl. No.: 55,402

[22] Filed: Apr. 30, 1993

Related U.S. Application Data

[60] Continuation of Ser. No. 678,382, Apr. 1, 1991, abandoned, which is a division of Ser. No. 584,398, Sep. 14, 1990, Pat. No. 5,066,808, which is a continuation of Ser. No. 419,428, Oct. 10, 1989, abandoned.

[30] Foreign Application Priority Data

Oct. 21, 1988 [JP] Japan .................. 63-264020
Mar. 13, 1989 [JP] Japan .................. 64-057813

[51] Int. Cl.$^6$ .................. C07D 277/32; A01N 43/78
[52] U.S. Cl. .................. 514/365; 514/155; 514/326; 544/369; 546/209; 548/202; 548/203; 548/204; 548/205

[58] Field of Search .................. 544/374; 548/131, 143, 548/203, 205, 247, 343, 378, 202, 204; 549/74, 75; 514/255, 364, 365, 378, 399, 406, 438, 326; 546/209

[56] References Cited

U.S. PATENT DOCUMENTS

5,063,236  11/1991  Gsell .................. 514/318

FOREIGN PATENT DOCUMENTS

0235725  2/1987  European Pat. Off. .......... 548/205

*Primary Examiner*—C. Warren Ivy
*Assistant Examiner*—Zinna N. Davis
*Attorney, Agent, or Firm*—Sprung Horn Kramer & Woods

[57] ABSTRACT

A cyano compound useful as an insecticide, of the formula (I)

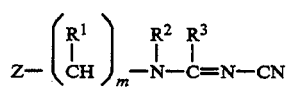

wherein the radicals are defined in the claims.

9 Claims, No Drawings

INSECTICIDALLY ACTIVE CYANO COMPOUNDS

This application is a continuation of application Ser. No. 678,382, filed Apr. 1, 1991 now abandoned, which is a division, of application Ser. No. 584,398 now U.S. Pat. No. 5,066,808, filed Sep. 14, 1990 which is a continuation application of Ser. No. 419,428, filed Oct. 10, 1989 now abandoned.

The present invention relates to novel cyano compounds, to processes for their preparation and to their use as insecticides.

It has already been disclosed that certain N-cyanoisothioureas are useful as medicaments for treating ulcers (see Japanese Patent Laid-open No. 234,064/1987), and that the N-cyanoisothioureas disclosed in the above Japanese patent application and other N-cyanoisothioureas have also a function for controlling insects and plant-destructive nematodes (see Japanese Patent Laid-open No. 233,903/1988 and EP-OS 303,570), and furthermore that certain N-cyanoguanidines have insecticidal function (see Japanese Patent Laid-open No. 47,766/1989).

There have now been found novel cyano compounds of the formula (I)

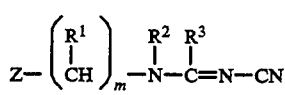
(I)

wherein $R^1$ is hydrogen, cyano or $C_{1-4}$ alkyl,
m is 0 or 1,
$R^2$ is hydrogen, $C_{1-6}$ alkyl, $C_{3-4}$ alkenyl optionally substituted by halogen,
$C_{3-4}$ alkynyl, $C_{3-8}$ cycloalkyl optionally substituted by methyl, optionally substituted phenyl, optionally substituted benzyl, hydroxy, $C_{1-4}$ alkoxy or —CH$_2$—Z, in which Z has the same meanings as stated below,
$R^3$ is —O—$R^4$, —S—$R^4$ or

in which $R^4$ is $C_{1-6}$ alkyl, $C_{3-4}$ alkenyl, $C_{3-4}$ alkynyl, $C_{3-8}$ cycloalkyl, optionally substituted phenyl, optionally substituted benzyl or
—(CH$_2$)n-Z, in which n is 1 or 2 and
Z has the same meanings as stated below, and
$R^5$ and $R^6$ are hydrogen, $C_{1-9}$ alkyl optionally substituted by at least one selected from a group consisting of halogen, hydroxy, mercapto, $C_{1-2}$ alkoxy, $C_{1-2}$ alkylthio, $C_{3-6}$ cycloalkyl, amino, $C_{1-2}$ monoalkylamino, $C_{2-4}$ (in total)di-alkylamino, carboxy, $C_{1-2}$ alkoxy-carbonyl and cyano, $C_{3-4}$ alkenyl optionally substituted by halogen, $C_{3-4}$ alkynyl, optionally substituted phenyl, optionally substituted benzyl, $C_{1-4}$ alkoxy, hydroxy, formyl, $C_{1-4}$ alkoxy-carbonyl, $C_{1-4}$ alkylamino, $C_{2-4}$ (in total)di-alkylamino, amino, acyl or

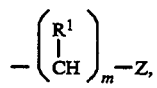

in which $R^1$ and m have the same meanings as stated above, and Z has the same meanings as stated below, and in addition,
$R^5$ and $R^6$ may form, together with the N-atom to which they are bonded, a 3 to 7 membered ring which may be substituted by $C_{1-2}$ alkyl and may contain N, O or S as the member of said ring, besides the N-atom to which they are bonded, and Z is a substituted 5 or 6 membered heterocyclic group which contains at least one heteroatom selected from N, O and S as a ring member, provided that where Z is pyridyl substituted by halogen, m is 1, $R^2$ is $C_{1-6}$ alkyl and $R^3$ is —S-alkyl($C_{1-6}$) or —S-benzyl, then $R^1$ is cyano or $C_{1-4}$ alkyl.

The compounds of the formula (I) can be obtained when
a) in the case where $R^3$ is —S—$R^4$; compounds of the formula (II)

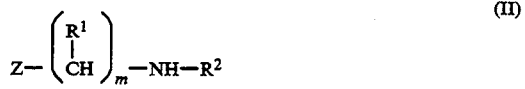
(II)

wherein $R^1$, m, $R^2$ and Z have the same meanings as stated above, are reacted with compounds of the formula (III)

(III)

wherein $R^4$ has the same meaning as stated above, in the presence of inert solvents, or
b) in the case where $R^3$ is —O—$R^4$; the aforesaid compounds of the formula (II) are reacted with compounds of the formula (IV)

(IV)

wherein $R^4$ has the same meaning as stated above, in the presence of inert solvents, or
c) in the case where $R^3$ is

the aforesaid compounds of the formula (II) are reacted with compounds of the formula (V)

(V)

wherein $R^4$, $R^5$ and $R^6$ have the same meanings as stated above, in the presence of inert solvents, or
d) in the case where $R^3$ is —S—$R^4$ and m is 1; compounds of the formula (VI)

(VI)

wherein $R^1$ and Z have the same meanings as stated above, and M is halogen, are reacted with compounds of the formula (VII)

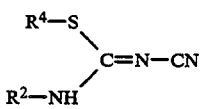
(VII)

wherein $R^2$ and $R^4$ have the same meanings as stated above, in the presence of inert solvents and if appropriate in the presence of a base.

The novel cyano compounds exhibit powerful insecticidal properties.

Surprisingly, the cyano compounds, according to the invention exhibit a substantially greater insecticidal function than those known from the aforementioned prior art.

Among the cyano compounds according to the invention, of the formula (I), preferred compounds are those in which $R^1$ is hydrogen or $C_{1-3}$ alkyl, m is 0 or 1, $R^2$ is hydrogen, $C_{1-4}$ alkyl, allyl, propargyl, phenyl optionally substituted by halogen, benzyloptionally substituted by halogen, hydroxy, $C_{1-3}$ alkoxy or —$CH_2$—$Z^1$ in which $Z^1$ is pyridyl optionally substituted by halogen, $R^3$ is —O—$R^4$, —S—$R^4$ or

in which $R^4$ is $C_{1-4}$ alkyl, allyl, propargyl, $C_{3-6}$ cycloalkyl, phenyl optionally substituted by halogen, benzyl optionally substituted by halogen or —$CH_2$—$Z^1$ in which $Z^1$ has the same meaning as stated above, $R^5$ and $R^6$ are hydrogen, $C_{1-9}$ alkyl optionally substituted by fluorine or chlorine, allyl optionally subsutituted by chlorine, propargyl, phenyl optionally substituted by chlorine, benzyl optionally substituted by chlorine, $C_{1-3}$ alkoxy, hydroxy, hydroxy-$C_{1-2}$ alkyl, mercapto-$C_{1-2}$ alkyl, amino-$C_{1-2}$ alkyl, $C_{1-3}$ alkylamino, dimethylamino, amino, cyano-$C_{1-2}$ alkyl, pyridyl optionally substituted by chlorine or methyl, or —$CH_2$—$Z^2$ in which $Z^2$ is pyridyl optionally substituted by halogen or 5-thiazolyl optionally substituted by halogen, and in addition, $R^5$ and $R^6$ may form, together with the N-atom to which they are bonded, a 3 to 6 membered ring which may be substituted by methyl and may contain N, O or S as the member of said ring, besides the N-atom to which they are bonded, and Z is a 5 membered heterocyclic group which is substituted by halogen or $C_{1-2}$ alkyl and contains one or two nitrogen atoms, or one nitrogen atom and either one oxygen atom or one sulfur atom, or a 6 membered heterocyclic group which is substituted by halogen or $C_{1-2}$ alkyl and contains one or two nitrogen atoms, provided that where Z is pyridyl substituted by halogen, m is 1, $R^2$ is $C_{1-4}$ alkyl and $R^3$ is —S-alkyl($C_{1-4}$) or —S-benzyl, then $R^1$ is $C_{1-3}$ alkyl.

Very particularly preferred cyano compounds of the formula (I) are those in which $R^1$ is hydrogen, methyl, ethyl or propyl, m is 0 or 1

$R^2$ is hydrogen, methyl, ethyl, propyl, allyl, propargyl, phenyl optionally substituted by chlorine, hydroxy, methoxy, ethoxy or pyridylmethyl optionally substituted by chlorine, $R^3$ is —O—$R^4$, —S—$R^4$ or

in which $R^4$ is $C_{1-3}$ alkyl, allyl, propargyl, cyclohexyl, phenyl, benzyl optionally substituted by chlorine, pyridylmethyl optionally substituted by chlorine, $R^5$ and $R^6$ are hydrogen, $C_{1-4}$ alkyl optionally substituted by fluorine or chlorine, allyl optionally substituted by chlorine, propargyl, phenyl optionally substituted by chlorine, benzyl optionally substituted by chlorine, methoxy, hydroxy, hydroxyethyl, $C_{1-2}$ alkylamino, dimethylamino, amino, cyanoethyl, 2-chloro-5-pyridylmethyl or 2-chloro-5-thiazolylmethyl, and in addition, $R^5$ and $R^6$ may form, together with the N-atom to which they are bonded, pyrrolidino, piperidino, 2-methylpiperidino, morpholine, piperazino or isoxazolidino, and Z is a 5 membered heterocyclic group which is substituted by halogen or $C_{1-2}$ alkyl and contains one or two nitrogen atoms, or one nitrogen atom and either one oxygen atom or one sulfur atom, or a 6 membered heterocyclic group which is substituted by halogen or $C_{1-2}$ alkyl and contains one or two nitrogen atoms, provided that where Z is pyridyl substituted by halogen, m is 1, $R^2$ is methyl, ethyl or propyl and $R^3$ is —S-alkyl($C_{1-3}$) or —S-benzyl, then $R^1$ is methyl, ethyl or propyl.

Specifically, the following compounds may be mentioned:

S-methyl-N-(2-chloro-5-pyridylmethyl)-N'-cyanoisothiourea,

S-methyl-N-(2-chloro-5-thiazolylmethyl)-N'-cyanoisothiourea, 3-(2-chloro-5-pyridylmethyl)-3-methyl-2-cyanoguanidine, 3-(2-chloro-5-pyridylmethyl)-1-methyl-2-cyanoguanidine, 3-(2-chloro-5-pyridylmethyl)-1,1-dimethyl-2-cyanoguanidine, 3-(2-chloro-5-pyridylmethyl)-1,3-dimethyl-2-cyanoguanidine, 3-(2-chloro-5-pyridylmethyl)-1,1,3-trimethyl-2-cyanoguanidine, and 1,3-bis(2-chloro-5-pyridylmethyl)-2-cyanoguanidine.

If, for example, in the process a), 5-aminomethyl-2-chloropyridine and dimethyl cyanamidodithiocarbonate are used as starting materials, the course of the reaction can be represented by the following equation:

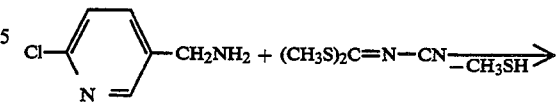

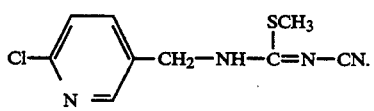

If, for example, in the process b), 5-aminomethyl-2-chloropyridine and diethyl cyanamidocarbonate are used as starting materials, the course of the reaction can be represented by the following equation:

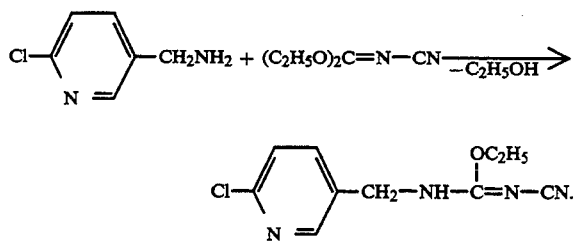

If, for example, in the process c), 5-aminomethyl-2-chloropyridine and 3-cyano-1-methyl-2-methylisothiourea are used as starting materials, the course of the reaction can be represented by the following equation:

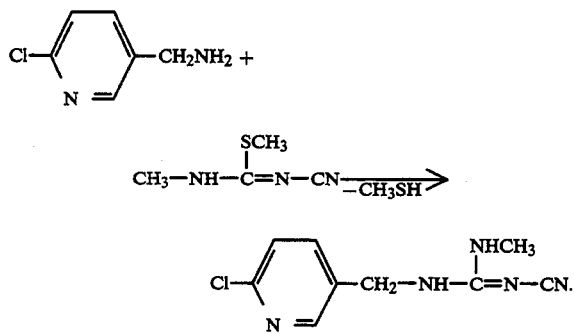

If, for example, in the process d), 2-chloro-5-chloromethylthiazole and 3-cyano-2-methylisothiourea are used as starting materials, the course of the reaction can be represented by the following equation:

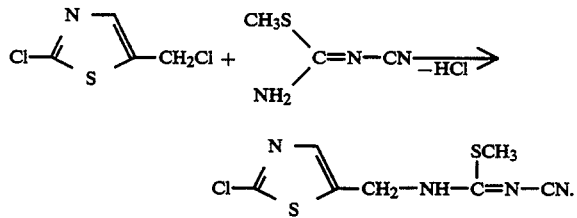

In the process a), the compounds of the formula (II) as a starting material mean ones based on the aforementioned definitions of $R^1$, m, $R^2$ and Z.

In the formula (II), $R^1$, m, $R^2$ and Z have preferably the same meanings as already given above.

The compounds of the formula (II) include known compounds which have been described in U.S. Pat. No. 4,499,907 and Nihon Kagaku Zasshi (Periodical of Japanese Chemistry), vol. 83, pp. 218–222, 1962, and as examples thereof, there may be mentioned:
5-aminomethyl-2-chloropyridine,
5-aminomethyl-2-chlorothiazole and
5-methylaminomethyl-2-chloropyridine.

The compounds of the formula (III), as also a starting material in the process a), mean ones based on the aforementioned definition of $R^4$.

In the formula (III), $R^4$ has preferably the same meaning as already given above.

The compounds of the formula (III) are known compounds described in for instance Japanese Patent Publication No. 26,482/1969, and as examples, cyanamidodithio dimethylcarbonate may be exemplified.

In the process b), the compounds of the formula (IV) as a starting material mean ones based on the aforementioned definition of $R^4$.

In the process b), $R^4$ has preferably the same meaning as already given above.

The compounds of the formula (IV) are known compounds described in Japanese Patent Laid-open No. 126,856/1988, and as examples, cyanamido diethylcarbonate may be exemplified.

In the process c), the compounds of the formula (V) as a starting material mean ones based on the aforementioned definitions of $R^4$, $R^5$ and $R^6$.

In the formula (V), $R^4$, $R^5$ and $R^6$ have preferably the same meanings as already given above.

The compounds of the formula (V) may be obtained in general when the aforementioned compounds of the formula (III) are reacted with compounds of the formula (VIII)

wherein $R^5$ and $R^6$ have the same meanings as stated above, in the presence of inert solvents.

The above compounds of the formula (VIII) are well-known in organic chemistry.

In the process d), the compounds of the formula (VI) as a starting material mean ones based on the aforementioned definitions of $R^1$, Z and M.

In the formula (VI), $R^1$ and Z have preferably the same meanings as already given above, and M preferably represents chlorine or bromine.

The compounds of the formula (VI) are known compounds described in Japanese Patent Laid-open No. 81,382/1987, and as examples, there may be mentioned:
2-chloro-5-chloromethylthiazole and
2-chloro-5-chloromethylpyridine.

The compounds of the formula (VII), as also a starting material in the process d), mean ones based on the aforementioned definitions of $R^2$ and $R^4$.

In the formula (VII), $R^2$ and $R^4$ have preferably the same meanings as already given above.

The compounds of the formula (VII), in the same way as the above process for the preparation of the compounds of the formula (V), may be obtained when the aforementioned compounds of the formula (III) are reacted with compounds of the formula (IX)

wherein $R^2$ has the same meaning as stated above, in the presence of inert solvents, The above compounds of the formula (IX) are well-known.

Suitable diluents in the process a) are all inert organic solvents.

As examples of such solvents, these preferentially include water; aliphatic, cycloaliphatic and aromatic, optionally chlorinated, hydrocarbons, such as hexane, cyclohexane, petroleum ether, ligroin, benzene, toluene, xylene, methylene chloride, chloroform, carbon tetrachloride, ethylene chloride, trichloroethylene, chlorobenzene and the like; ethers such as diethyl ether, methyl ethyl ether, di-isopropyl ether, dibutyl ether, propylene oxide, dioxane, tetrahydrofuran and the like; ketones such as acetone, methylethyl ketone, methyl-iso-propyl ketone, methyl-iso-butyl ketone; nitriles such as acetonitrile, propionitrile, acrylonitrile and the like; alcohols such as methanol, ethanol, iso-propanol, butanol, ethylene glycol and the like; esters such as ethyl acetate, amyl acetate; acid amides such as dimethyl formamide, dimethyl acetamide and the like; and sulfones and sulfoxides such as dimethyl sulfoxide, sulfolane and the like; and bases, for example, such as pyridine.

The reaction temperature of the process a) can be varied within a substantial range.

In general, the reaction is carried out at between about 0° and about 150° C., preferably between about 20° C. and about 100° C.

The reaction of the process a) can be carried out under normal, elevated or reduced pressure.

In carrying out the process a), for example, about 1 to 1.2 moles, preferably 1.1 moles of the compounds of the formula (III) may be employed per mole of the compounds of the formula (II), and these compounds are reacted in the presence of inert solvents, for example, alcohol, until the generation of mercaptan has ceased so that the desired compounds of the formula (I) can be obtained.

In carrying the process b), suitable diluents include the same solvents as exemplified for the process a).

The reaction temperatures of the process b) can be varied within a substantial range. In general, the reaction is carried out at between about 0° and about 150° C., preferably between 20° C. and about 80° C.

The reaction of the process b) can be carried out under normal, elevated or reduced pressure.

In carrying out the process b), for example, about 1 to 1.2 moles, preferably about 1 to 1.1 moles of the compounds of the formula (IV) may be employed per mole of the compounds of the formula (II), and these compounds are reacted in the presence of inert solvents, for example, alcohol, so that the desired compounds of the formula (I) can be obtained.

In carrying the process c), suitable diluents include the same solvents as exemplified for the process a).

The reaction temperatures of the process c) can be varied within a substantial range. In general, the reaction is carried out at between about 0° and about 150° C., preferably between 20° C. and about 100° C.

The reaction of the process c) can be carried out under normal, elevated or reduced pressure.

In carrying out the process c), for example, about 1 to 1.2 moles, preferably about 1 to 1.1 moles of the compounds of the formula (V) may be employed per mole of the compounds of the formula (II), and these compounds are mixed up during heating, so that the desired compounds of the formula (I) can be obtained.

In carrying the process d), suitable diluents include the same solvents as exemplified for the process a), as well as ketones, such as acetone, methylethyl ketone, methylisopropyl ketone, and methyl iso-butyl ketone.

The process d) can be carried out in the presence of a base.

As examples of bases, these preferentially include, for example, potassium hydroxide, sodium hydroxide, sodium hydride, sodium carbonate, potassium carbonate, sodium methoxide, sodium ethoxide, potassium tert-butoxide, and tert-amines such as triethylamine, diethylaniline, pyridine and the like.

The reaction temperatures of the process d) can be varied within a substantial range. In general, the reaction is carried out at between about 0 and boiling point of the reaction mixture is preferably between about 0° and about 80° C.

The reaction of the process d) can be carried out under normal, elevated or reduced pressure.

In carrying out the process d), for example, about 0.8 to 1.2 moles, preferably about 0.9 to 1.1 moles of the compounds of the formula (VII) may be employed per mole of the compounds of the formula (VI), and these compounds are reacted in the presence of inert solvents, for example, dimethylsulfoxide, so that the desired compounds of the formula (I) can be obtained.

The active compounds are well tolerated by plants, have a favorable level of toxicity to warm-blooded animals, and can be used for combating arthropod pests, especially insects which are encountered in agriculture, in forestry, in the protection of stored products and of materials, and in the hygiene field. They are active against normally sensitive and resistant species and against all or some stages of development. The above-mentioned pests include:

from the class of the Isopoda, for example Oniscus Asellus, *Armadillidium vulgare* and *Porcellio scaber;* from the class of the Diplopoda, for example, *Blaniulus guttulatus;* from the class of the Chilopoda, for example, *Geophilus carpophagus* and Scutigera spec.;

from the class of the Symphyla, for example, *Scutigerella immaculata;* from the order of the Thysanura, for example, *Lepisma saccharina;* from the order of the Collembola, for example, *Onychiurus armatus;* from the order of the Orthoptera; for example, *Blatta orientalis, Periplaneta americana, Leucophaea maderae, Blattella germanica, Acheta domesticus,* Gryllotalpa spp., *Locusta migrato ria migratorioides, Melanoplus differentialis* and *Schistocerca gregaria;* from the order of the Dermaptera, for example, *Forficula auricularia;* from the order of the Isoptera, for example, Reticulitermes spp.;

from the order of the Anoplura, for example, *Phylloxera vastatrix,* Pemphigus spp., *Pediculus humanus corporis,* Haematopinus spp. and Linognathus spp.;

from the order of the Mallophaga, for example, Trichodectes spp. and Damalinea spp.;

from the order of the Thysanoptera, for example, *Hercinothrips femoralis* and *Thrips tabaci,* from the order of the Heteroptera, for example, Eurygaster spp., *Dysdercus intermedius, Piesma quadrata, Cimex lectularius,* Rhodnius prolixus and Triatoma spp.;

from the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis,* Macrosi-

*phum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.;

from the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Spodoptera exiqua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana*;

from the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*,Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus ssp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica*;

from the order of the Hymenoptera for example, Diprion spp., Hoplocampa spp., Lasius spp., *Monomorium pharaonis* and Vespa spp.;

from the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*;

from the order of the Siphonaptera, for example, *Xenopsylla cheopis* and Ceratophyllus spp.;

from the class of the Arachnida, for example, *Scorpio maurus* and *Latrodectus mactans*;

from the order of the Aranina, for example *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The plant-parasitic nematodes include Pratylenchus spp., *Radopholus similis, Ditylenchus dipsaci, Tylenchulus semipenetrans*, Heterodera spp., Meloidogyne spp., Aphelenchoides spp., Longidorus spp., Xiphinema spp., and Trichodorus spp.

Furthermore, in the field of veterinary medicine, the novel compound of the present invention can effectively be employed for combating a variety of noxious animal-parasitic pests (internal-and external-parasitic pests), e.g., parasitic insects and nemotodes. Such animal-parasitic pests may be exemplified as follows:

From the class of Insecta, e.g., Gastrophilus spp., Stomoxys spp., Tricodectes spp., Rhodnius spp., *Ctenocephalides canis* and the like.

The active compounds can be converted into the customary formulations, such as solutions, emulsions, wet-table powders, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example, by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic hydrocarbons, such as cyclohexane or paraffins, for example, mineral oil fractions, alcohols, such as butanol or glycol, as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example, aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example, alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example, iron oxide, titanium oxide and Prussian Blue, and organic dyestuffs, such as alizarin dyestuffs, azo dyestuffs or metal phthalocyanine dyestuffs, and trace nutrients, such as salts of iron, manganese boron, copper, cobalt, molybdenum and zinc.

The formulations in general contain from 0.1 to 95 percent by weight of active compound, preferably from 0.5 to 90 percent by weight.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay, as well as a good stability to alkali on limed substrates.

The preparation and use of the active compounds according to the invention can be seen from the following non-limiting examples.

EXAMPLES OF PREPARATION

Example 1

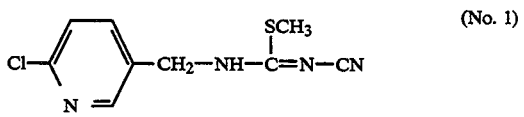
(No. 1)

5-aminomethyl-2-chloropyridine (1.43 g) and cyanamidedithio dimethyl carbonate (1.46 g) were dissolved in methanol (20 ml), while the solution was refluxed under heating for six hours.

After being allowed to cool, the separated crystals were filtered to obtain the desired S-methyl-N-(2-chloro-5-pyridylmethyl)-N'-cyanoisothiourea (1.2 g) having a melting point of from 191° to 194° C.

Example 2

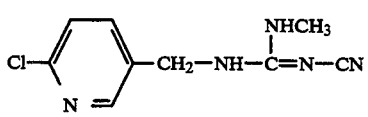

A mixture of 3-cyano-1-methyl-2-methylisothiourea (0.65 g) and 5-aminomethyl-2-chloropyridine (0.72 g) was stirred under heating at 100° C. for three hours. Then, the reaction product was cooled to room temperature and then purified on silica gel column chromatography (eluent: ethanol/chloroform) to obtain the desired 3-(2-chloro-5-pyridylmethyl)-1-methyl-2-cyanoguanidine (0.5 g) having a melting point in the range of from 193° to 197° C.

Example 3

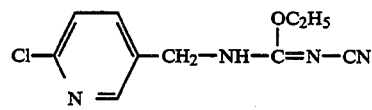

A mixture of 5-aminomethyl-2-chloropyridine (1.6 g), cyanamide dimethyl carbonate (1.6 g) and ethanol (30 ml) was refluxed under heating for four hours. Then, under reduced pressure, the ethanol contained in the reaction product was distilled off therefrom, followed by purification of the residue on silica gel chromatography (eluent: ethanol/chloroform) to obtain the desired O-ethyl-N-(2-chloro-5-pyridylmethyl)-N'-cyanoisothiourea (1.7 g) having a melting point in the range of from 161° to 164° C.

Example 4

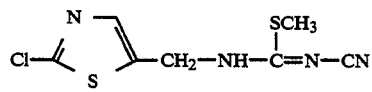

To a solution of 3-cyano-2-methylisothiourea (1.0 g) in dimethylformamide (30 ml) was portion wise added sodium hydride (0.22 g) at a temperature of from 0° to 5° C., followed by stirring for one hour. Thereafter, 2-chloro-5-chloromethylthiazole (1.5 g) was added to the solution obtained above at a temperature of from 5° to 10° C., followed by an overnight stirring at room temperature.

After the dimethylformamide contained in the solution had been distilled off under reduced pressure therefrom, the residue was washed with hexane, water, and chloroform in that order to obtain the desired S-methyl-N-(2-chloro-5-thiazolylmethyl)-N'-cyano-isothiourea (0.4 g) having a melting point in the range of from 167° to 171° C.

Example 5

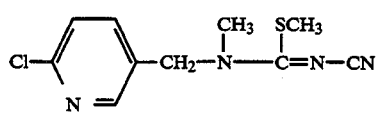

5-Aminomethyl-2-chloropyridine (1.57 g) and cyanamidedithio dimethyl carbonate (1.46 g) were dissolved in methanol (10 ml), while the solution was refluxed under heating for ten hours.

After being allowed to cool, the ethanol contained therein was distilled off from the solution and the thus obtained residue was purified on silica gel column chromatography (eluent: ethanol/chloroform) to obtain the desired S,N-dimethyl-N-(2-chloro-5-chloropyridylmethyl)-N'-cyanoisothiourea (1.0 g) having $n_D^{20}$ 1.6212.

Together with the compounds prepared in Example 1 to Example 5, other compounds that can be obtained in the same way as said Examples are shown in the following Table 1:
TABLE 1
$$Z-\left(\begin{array}{c}R^1\\|\\CH\end{array}\right)_m-\overset{R^2}{\underset{|}{N}}-\overset{R^3}{\underset{|}{C}}=N-CN$$
| Comp. No. | Z | R¹ | m | R² | R³ | Physical property |
|---|---|---|---|---|---|---|
| 1 | 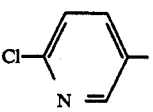 | H | 1 | H | SCH₃ | mp. 191–194° C. |
| 2 | 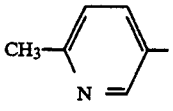 | H | 1 | H | SCH₃ | |
| 3 | 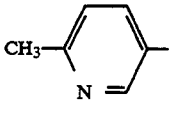 | H | 1 | CH₃ | SCH₃ | |
| 4 | 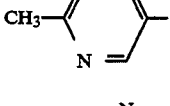 | H | 1 | C₂H₅ | SCH₃ | |
| 5 | 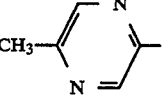 | H | 1 | H | SCH₃ | mp. 163–166° C. |
| 6 | 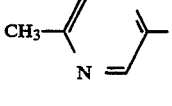 | CH₃ | 1 | H | SCH₃ | |
| 7 | 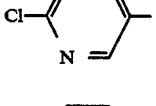 | H | 1 | CH₃ | SCH₃ | $n_D^{20}$ 1.6212 |
| 8 | 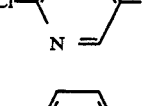 | CH₃ | 1 | H | SCH₃ | $n_D^{20}$ 1.5895<br>mp. 135–138° C. |
| 9 | 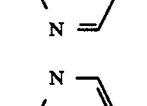 | H | 1 | 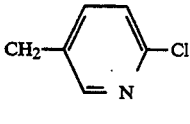 | SCH₃ | $n_D^{20}$ 1.6285 |
| 10 | 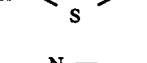 | H | 1 | H | SCH₃ | mp. 167–171° C. |
| 11 | 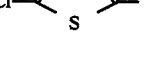 | H | 1 | CH₃ | SCH₃ | |
| 12 | 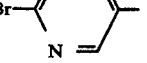 | H | 1 | H | SCH₃ | |

TABLE 1-continued
$$Z-\left(\begin{array}{c}R^1\\|\\CH\end{array}\right)_m-\overset{R^2}{\underset{}{N}}-\overset{R^3}{\underset{}{C}}=N-CN$$
| Comp. No. | Z | R$^1$ | m | R$^2$ | R$^3$ | Physical property |
|---|---|---|---|---|---|---|
| 13 | 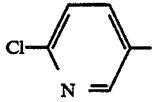 | — | 0 | H | SCH$_3$ | mp. 139–142° C. |
| 14 | 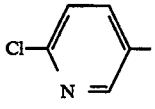 | H | 1 | C$_2$H$_5$ | SCH$_3$ | |
| 15 | 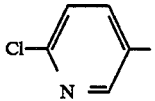 | H | 1 | C$_3$H$_7$-n | SCH$_3$ | |
| 16 | 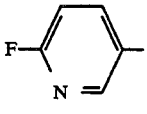 | H | 1 | C$_3$H$_7$-iso | SCH$_3$ | |
| 17 | 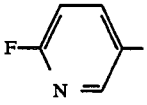 | CH$_3$ | 1 | C$_4$H$_9$-n | SCH$_3$ | |
| 18 | 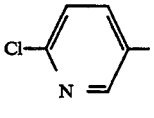 | H | 1 | CH$_2$C≡CH | SCH$_3$ | n$_D^{20}$ 1.6178 |
| 19 | 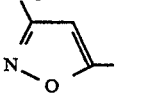 | H | | H | SCH$_3$ | |
| 20 | 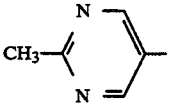 | H | | H | SCH$_3$ | |
| 21 | 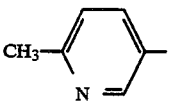 | H | | H | SC$_2$H$_5$ | |
| 22 | 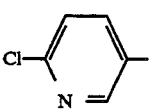 | H | | H | SC$_2$H$_5$ | mp. 152–153.5° C. |
| 23 | 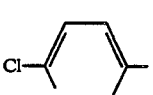 | H | | CH$_3$ | SC$_2$H$_5$ | |
| 24 | 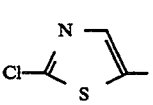 | H | | H | SC$_2$H$_5$ | |

TABLE 1-continued $$Z-\left(\begin{array}{c}R^1\\|\\CH\end{array}\right)_m-\overset{R^2}{\underset{|}{N}}-\overset{R^3}{\underset{|}{C}}=N-CN$$

| Comp. No. | Z | $R^1$ | m | $R^2$ | $R^3$ | Physical property |
|---|---|---|---|---|---|---|
| 25 | Cl-thiazole (N,S) | — | 0 | H | $SCH_3$ | |
| 26 | CF₃-thiazole (N,S) | $C_3H_7$-n | 1 | H | $SC_2H_5$ | |
| 27 | Cl-pyridyl | H | 1 | H | $SC_3H_7$-n | mp. 141.5–143° C. |
| 28 | $CH_3$-pyridyl | H | 1 | $CH_3$ | $SC_3H_7$-n | |
| 29 | Cl-pyridyl | H | 1 | H | $SC_3H_7$-n | |
| 30 | Cl-pyridyl | H | 1 | H | $SC_4H_9$-n | |
| 31 | Cl-pyridyl | H | 1 | $CH_3$ | $SC_4H_9$-n | |
| 32 | Cl-thiazole (N,S) | H | 1 | H | $SCH_2CH=CH_2$ | |
| 33 | Cl-pyridyl | H | 1 | H | $S-CH_2$-(6-Cl-pyridyl) | |
| 34 | Cl-pyridyl | H | 1 | $CH_3$ | $S-CH_2$-(6-Cl-pyridyl) | |
| 35 | Cl-pyridyl | H | 1 | H | $S$-phenyl | |
| 36 | Cl-pyridyl | $CH_3$ | 1 | H | $S$-(4-Cl-phenyl) | |

TABLE 1-continued

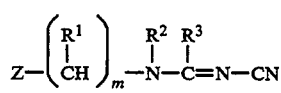

| Comp. No. | Z | $R^1$ | m | $R^2$ | $R^3$ | Physical property |
|---|---|---|---|---|---|---|
| 37 | CF$_3$-pyridin-5-yl (2-position) | C$_2$H$_5$ | 1 | H | OCH$_3$ | |
| 38 | 2-Br-pyridin-5-yl | H | 1 | C$_2$H$_5$ | OCH$_3$ | |
| 39 | 2-Cl-pyridin-5-yl | H | 1 | H | OCH$_3$ | mp. 204–207° C. |
| 40 | 2-Cl-pyridin-5-yl | H | 1 | CH$_3$ | OCH$_3$ | $n_D^{20}$ 1.5755 |
| 41 | 2,3-diCl-pyridin-5-yl | H | 1 | CH$_3$ | OCH$_3$ | |
| 42 | 2-Cl-pyrimidin-5-yl | H | 1 | H | OCH$_3$ | |
| 43 | 2-CH$_3$-pyrazin-5-yl | H | 1 | C$_3$H$_7$-n | OCH$_3$ | |
| 44 | 3-CF$_3$-pyridazin-6-yl | H | 1 | H | OC$_2$H$_5$ | |
| 45 | 2-Cl-pyrimidin-5-yl | H | 1 | H | OC$_2$H$_5$ | |
| 46 | 2-Cl-pyridin-5-yl | H | 1 | H | OC$_2$H$_5$ | mp. 161–164° C. |
| 47 | 2-Cl-pyridin-5-yl | H | 1 | CH$_3$ | OC$_2$H$_5$ | |

TABLE 1-continued $$Z-\left(\underset{CH}{\overset{R^1}{|}}\right)_m-\underset{|}{\overset{R^2}{N}}-\underset{|}{\overset{R^3}{C}}=N-CN$$

| Comp. No. | Z | $R^1$ | m | $R^2$ | $R^3$ | Physical property |
|---|---|---|---|---|---|---|
| 48 | 2-fluoropyridin-5-yl | H | 1 | H | $OC_3H_7$-n | |
| 49 | 2-methylpyrimidin-5-yl | H | 1 | $C_2H_5$ | phenoxy (O–C₆H₅) | |
| 50 | 2-chloropyridin-5-yl | H | 1 | H | 4-chlorophenoxy | |
| 51 | 2-chloropyridin-5-yl | H | 1 | H | $O-CH_2$-(2-chloropyridin-5-yl) | |
| 52 | 2-trifluoromethylpyridin-5-yl | H | 1 | $CH_3$ | $O-CH_2$-(2-chloropyridin-5-yl) | |
| 53 | 3-methyl-isoxazol-5-yl | H | 1 | H | $O-CH_2$-(2-chloropyridin-5-yl) | |
| 54 | 2-chloropyridin-5-yl | H | 1 | H | $NH_2$ | mp. 142–145° C. |
| 55 | 2-chloropyridin-5-yl | H | 1 | $CH_3$ | $NH_2$ | mp. 169–173° C. |
| 56 | 2-chloropyridin-5-yl | — | 0 | H | $NH_2$ | |
| 57 | 3-methyl-1,2,4-oxadiazol-5-yl | H | 1 | $C_3H_7$-n | $NH_2$ | |
| 58 | 3-methyl-isoxazol-5-yl | $CH_3$ | 1 | H | $NH_2$ | |
| 59 | 2-methylpyridin-5-yl | $C_4H_9$-n | 1 | H | $NH_2$ | |

TABLE 1-continued $$Z-\left(\begin{array}{c}R^1\\|\\CH\end{array}\right)_m-\overset{R^2}{N}-\overset{R^3}{C}=N-CN$$

| Comp. No. | Z | $R^1$ | m | $R^2$ | $R^3$ | Physical property |
|---|---|---|---|---|---|---|
| 60 | 2-chloro-thiazol-5-yl | H | 1 | $CH_3$ | $NH_2$ | |
| 61 | 1-methyl-pyrazol-4-yl | H | 1 | H | $NHCH_3$ | |
| 62 | 6-chloro-pyridin-3-yl | H | 1 | H | $NHCH_3$ | mp. 193–197° C. |
| 63 | 6-chloro-pyridin-3-yl | H | 1 | $CH_3$ | $NHCH_3$ | mp. 113–118° C. |
| 64 | 6-chloro-pyridin-3-yl | — | 0 | H | $NHCH_3$ | |
| 65 | 6-cyano-pyridin-3-yl | $CH_3$ | 1 | $CH_3$ | $NHCH_3$ | |
| 66 | 6-fluoro-pyridin-3-yl | H | 1 | H | $NHCH_3$ | |
| 67 | 6-bromo-pyridin-3-yl | H | 1 | $CH_3$ | $NHCH_3$ | |
| 68 | 6-methyl-pyridin-3-yl | H | 1 | H | $NHC_2H_5$ | |
| 69 | 6-chloro-pyridin-3-yl | H | 1 | H | $NHC_2H_5$ | mp. 135–137.5° C. |
| 70 | 2-chloro-thiazol-5-yl | H | 1 | H | $NHC_2H_5$ | |
| 71 | 6-chloro-pyridin-3-yl | H | 1 | $CH_3$ | $NHC_2H_5$ | $n_D^{20}$ 1.5756 |

TABLE 1-continued $$Z-\left(\begin{array}{c}R^1\\|\\CH\end{array}\right)_m-\overset{R^2}{\underset{|}{N}}-\overset{R^3}{\underset{|}{C}}=N-CN$$

| Comp. No. | Z | R¹ | m | R² | R³ | Physical property |
|---|---|---|---|---|---|---|
| 72 | 6-Cl-pyridin-3-yl | H | 1 | H | NHC₃H₇-n | |
| 73 | 6-Cl-pyridin-3-yl | H | 1 | C₄H₉-n | NHC₃H₇-n | |
| 74 | 3-CH₃-pyrazin-6-yl | H | 1 | H | NHC₃H₇-iso | |
| 75 | 2-Cl-pyrimidin-5-yl | H | 1 | CH₃ | NHC₃H₇-iso | |
| 76 | 6-Cl-pyridin-3-yl | H | 1 | H | NHC₄H₉-n | |
| 77 | 6-Cl-pyridin-3-yl | H | 1 | CH₃ | NHC₄H₉-n | |
| 78 | 6-Cl-pyridin-3-yl | H | 1 | H | NHCH₂CH(OCH₃)₂ | |
| 79 | 6-Cl-pyridin-3-yl | H | 1 | H | NHCH₂CF₃ | |
| 80 | 6-Cl-pyridin-3-yl | H | 1 | CH₃ | NHCH₂CF₃ | |
| 81 | 6-Cl-pyridin-3-yl | H | 1 | H | NHCH₂CH=CH₂ | |
| 82 | 6-Cl-pyridin-3-yl | H | 1 | CH₃ | NHCH₂CH=CH₂ | |
| 83 | 2-Cl-thiazol-5-yl | H | 1 | H | NHCH₂CH=CH₂ | |

TABLE 1-continued $$Z-\left(\begin{array}{c}R^1\\|\\CH\end{array}\right)_m-\overset{R^2}{\underset{|}{N}}-\overset{R^3}{\underset{|}{C}}=N-CN$$

| Comp. No. | Z | R¹ | m | R² | R³ | Physical property |
|---|---|---|---|---|---|---|
| 84 | 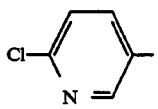 | H | 1 | H | NHCH₂C≡CH | |
| 85 | 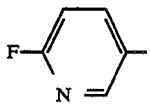 | H | 1 | H | NHCH₂CN | |
| 86 | 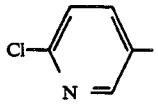 | H | 1 | H | NHCH₂CN | |
| 87 | 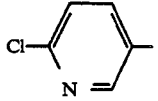 | H | 1 | CH₃ | NHCH₂CN | |
| 88 | 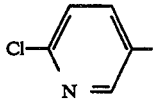 | H | 1 | H | NHCH₂CH₂CN | |
| 89 | 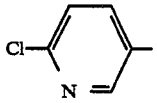 | H | 1 | H | NHCH₂CH₂NHCH₃ | |
| 90 | 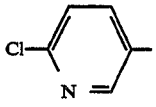 | H | 1 | CH₃ | NHCH₂CH₂N(CH₃)₂ | |
| 91 | 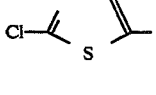 | H | 1 | CH₃ | 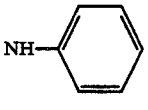 | |
| 92 | 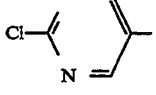 | H | 1 | H | 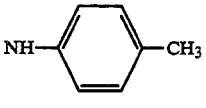 | |
| 93 | 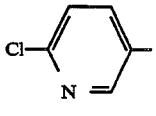 | H | 1 | H | 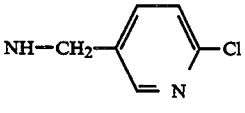 | mp. 149–153° C. |
| 94 | 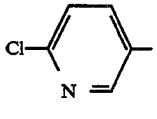 | CH₃ | 1 | H | 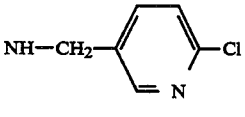 | |
| 95 | 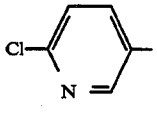 | H | 1 | CH₃ | 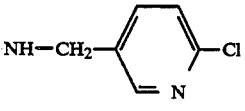 | mp. 123–128° C. |

TABLE 1-continued $$Z-\left(\begin{matrix}R^1\\|\\CH\end{matrix}\right)_m-\overset{R^2}{\underset{}{N}}-\overset{R^3}{\underset{}{C}}=N-CN$$

| Comp. No. | Z | R¹ | m | R² | R³ | Physical property |
|---|---|---|---|---|---|---|
| 96 | 2-Cl-5-pyridyl | CH₃ | 1 | CH₃ | NH—CH₂—(6-Cl-3-pyridyl) | |
| 97 | 2-Cl-5-pyridyl | H | 1 | H | NH—CH₂—(4-Cl-phenyl) | mp. 217–221° C. |
| 98 | 2-F-5-pyridyl | H | 1 | CH₃ | N(CH₃)₂ | |
| 99 | 2-Cl-5-pyridyl | H | 1 | H | N(CH₃)₂ | n$_D^{20}$ 1.5703 |
| 100 | 2-Cl-5-pyridyl | — | 0 | H | N(CH₃)₂ | |
| 101 | 2-Cl-5-thiazolyl | H | 1 | H | N(CH₃)₂ | |
| 102 | 6-Cl-2-pyridyl | H | 1 | H | N(CH₃)₂ | |
| 103 | 2-Cl-5-pyridyl | H | 1 | CH₂C≡CH | N(CH₃)₂ | |
| 104 | 2-Cl-5-pyridyl | H | 1 | H | N(CH₃)C₂H₅ | |
| 105 | 3-CH₃-5-isoxazolyl | H | 1 | H | N(CH₃)C₃H₇-n | |
| 106 | 2-CH₃-5-pyrimidinyl | H | 1 | CH₃ | N(CH₃)CH₂CH=CH | |

TABLE 1-continued $$Z-\left(\overset{R^1}{\underset{CH}{|}}\right)_m-\overset{R^2}{\underset{|}{N}}-\overset{R^3}{\underset{|}{C}}=N-CN$$

| Comp. No. | Z | R¹ | m | R² | R³ | Physical property |
|---|---|---|---|---|---|---|
| 107 | 6-Cl-pyridin-3-yl | H | 1 | H | N(CH₃)CH₂C≡CH | |
| 108 | 6-Cl-pyridin-3-yl | CH₃ | 1 | H | N(CH₃)(3-Cl-phenyl) | |
| 109 | 2-Cl-oxazol-5-yl | H | 1 | H | N(CH₃)CH₂(phenyl) | |
| 110 | 6-Cl-pyridin-3-yl | H | 1 | 2-methylcyclohexyl | N(C₂H₅)₂ | |
| 111 | 6-F-pyridin-3-yl | H | 1 | H | N(C₂H₅)₂ | |
| 112 | 2-Cl-thiazol-5-yl | — | 0 | H | N(C₂H₅)₂ | |
| 113 | 6-Cl-pyridin-3-yl | H | 1 | H | aziridin-1-yl | |
| 114 | 6-Cl-pyridin-3-yl | H | 1 | H | pyrrolidin-1-yl | |
| 115 | 2-Cl-thiazol-5-yl | H | 1 | phenyl | piperidin-1-yl | |
| 116 | 6-Cl-pyridin-3-yl | H | 1 | H | morpholin-4-yl | |
| 117 | 2,3-diCl-pyridin-5-yl | H | 1 | H | thiomorpholin-4-yl | |

TABLE 1-continued $$Z-\left(\begin{array}{c}R^1\\|\\CH\end{array}\right)_m-\overset{R^2}{\underset{}{N}}-\overset{R^3}{\underset{}{C}}=N-CN$$

| Comp. No. | Z | R¹ | m | R² | R³ | Physical property |
|---|---|---|---|---|---|---|
| 118 | 2-chloro-thiazol-5-yl | H | 1 | CH₃ | —N(piperazin-1-yl)NH | |
| 119 | 6-chloro-pyridin-3-yl | H | 1 | H | —N(4-methylpiperazin-1-yl)N—CH₃ | |
| 120 | 6-chloro-pyridin-3-yl | H | 1 | CH₃ | NHOCH₃ | |
| 121 | 6-chloro-pyridin-3-yl | H | 1 | H | NHNH₂ | |
| 122 | 6-chloro-pyridin-3-yl | H | 1 | CH₃ | NHNHCH₃ | |
| 123 | 6-chloro-pyridin-3-yl | H | 1 | H | NHN(CH₃)₂ | |
| 124 | 6-chloro-pyridin-3-yl | H | 1 | CH₃ | NHOH | |
| 125 | 6-chloro-pyridin-3-yl | H | 1 | H | NHCH₂C(Cl)=CH₂ | |
| 126 | 5,6-dimethyl-pyridin-3-yl | H | 1 | 4-NO₂-C₆H₄ | NHCH₃ | |
| 127 | 6-chloro-pyridin-3-yl | CN | 1 | H | SCH₃ | |
| 128 | 6-chloro-pyridin-3-yl | CN | 1 | CH₃ | SCH₃ | |
| 129 | 6-chloro-pyridin-3-yl | CN | 1 | H | OCH₃ | |

TABLE 1-continued $$Z-\left(\underset{CH}{\overset{R^1}{|}}\right)_m-\underset{|}{N}-\underset{}{\overset{R^2}{C}}=\underset{}{\overset{R^3}{N}}-CN$$

| Comp. No. | Z | $R^1$ | m | $R^2$ | $R^3$ | Physical property |
|---|---|---|---|---|---|---|
| 130 | 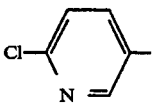 | CN | 1 | H | NHCH$_3$ | |
| 131 | 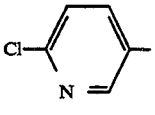 | H | 1 | CH$_2$CH=CHCl | SCH$_3$ | |
| 132 | 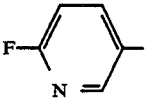 | H | 1 | H | NHC$_4$H$_9$-n | |
| 133 | 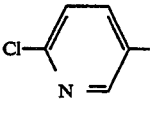 | H | 1 | H | NHCH$_2$CH$_2$OH | |
| 134 | 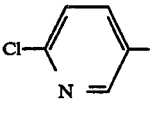 | H | 1 | CH$_3$ | NHCH$_2$CH$_2$SH | |
| 135 | 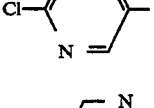 | H | 1 | CH | NHCH$_2$CH$_2$NH$_2$ | |
| 136 | 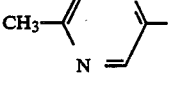 | H | 1 | H | NHCH$_2$CH$_2$Cl | |
| 137 | 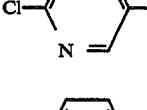 | H | 1 | CH$_3$ | NH(CH$_2$)$_3$COOH | |
| 138 | 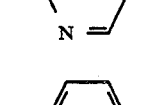 | H | 1 | H | NHCOOCH$_3$ | |
| 139 | 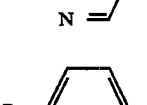 | H | 1 | C$_2$H$_5$ | NHCOOC$_2$H$_5$ | |
| 140 | 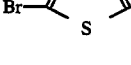 | H | 1 | H | SCH$_3$ | |
| 141 | 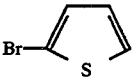 | H | 1 | CH$_3$ | SCH$_3$ | |

TABLE 1-continued $$Z-\left(\begin{array}{c}R^1\\|\\CH\end{array}\right)_m-\overset{R^2}{\underset{|}{N}}-\overset{R^3}{\underset{|}{C}}=N-CN$$

| Comp. No. | Z | $R^1$ | m | $R^2$ | $R^3$ | Physical property |
|---|---|---|---|---|---|---|
| 142 | CH₃-isoxazole | H | 1 | H | SCH₃ | |
| 143 | CH₃-isoxazole | H | 1 | CH₃ | SCH₃ | |
| 144 | Cl-pyridyl | H | 1 | CH₃ | NHC₃H₇-n | |
| 145 | Cl-pyridyl | H | 1 | H | NHCH₂CH₂SCH₃ | |
| 146 | Cl-pyridyl | H | 1 | H | N(CH₃)CH₂CH₂SCH₃ | |

Biological Test

Comparative compound E-1

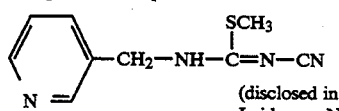

(disclosed in Japanese Patent Laid-open No. 233903/1988)

Comparative compound E-2

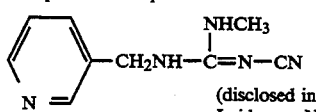

(disclosed in Japanese Patent Laid-open No. 47766/1989)

Example 6

Test on *Nephotettix cincticeps* having resistance to organophosphorus agents:

Preparation of a test chemical

Solvent: 3 parts by weight of xylene

Emulsifier: 1 part by weight of polyoxyethylene alkyl phenyl ether

To form a suitable preparation, 1 part by weight of the active compound was mixed with the aforesaid amount of the solvent containing the aforesaid amount of the emulsifier. The mixture was diluted with water to a predetermined concentration.

Testing method

Onto rice plants, about 10 cm tall, planted in pots each having a diameter of 12 cm was sprayed 10 ml per pot of the water-dilution of each active compound in a predetermined concentration prepared as above. The sprayed chemical was dried, and a wire net having a diameter of 7 cm and a height of 14 cm was put over each pot, and 30 female imagoes of *Nephotettix cincticeps* showing resistance to organophosphorus agents were released into the net. The pots were each placed in a constant temperature chamber and the number of dead insects was examined 2 days later, and the insect mortality was calculated.

The results are shown in Table 2.

TABLE 2

| Compound No. | Concentration of the active ingredient ppm | Insect mortality, % |
|---|---|---|
| 1 | 50 | 100 |
| 10 | 50 | 100 |
| 62 | 50 | 100 |
| 63 | 50 | 100 |
| 99 | 50 | 100 |
| Comparative | | |
| E-1 | 50 | 0 |
| E-2 | 50 | 20 |

Example 7

Test on planthoppers

Testing method

A water dilution in a predetermined concentration of the active compound prepared as in Example 6 was sprayed onto rice plants, about 10 cm tall, grown in pots with a diameter of 12 cm in an amount of 10 ml per pot. The sprayed chemical was dried, and a wire net, 7 cm in diameter and 14 cm tall, was put over each of the pots. Thirty female imagoes of *Milaparvata lugens* Stal of a strain which showed resistance to organophosphorus chemicals were released into the net. The pots were left to stand in a constant temperature chamber and the number of dead insects was examined two days later. The insect mortality was then calculated.

In the same way as above, the kill ratio was calculated on *Sogatella furcifera* Horvath and organophosphorus-resistant *Laodelphax striatellus* Fallen.

The results are shown in Table 3.

TABLE 3

| Compound No. | Concentration of the active ingredient ppm | Insect mortality, % | | |
|---|---|---|---|---|
| | | *Nilaparvata lugens* | *Laodelphax striatellus* | *Sogatella furcifera* |
| 1 | 50 | 100 | 100 | 100 |
| 62 | 50 | 100 | 100 | 100 |
| 63 | 50 | 100 | 100 | 100 |
| 99 | 50 | 100 | 100 | 100 |
| Comparative | | | | |
| E-1 | 50 | 0 | 0 | 0 |
| E-2 | 50 | 0 | 0 | 0 |

It will be appreciated that the instant specification and claims are set forth by way of illustration and not limitation, and that various modifications and changes may be made without departing from the spirit and scope of the present invention.

What is claimed is:

1. A cyano compound of the formula

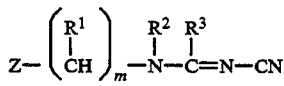
(I)

wherein

Z is thiazolyl substituted by halogen, $C_{1-2}$-alkyl, or $CF_3$ $R^1$ is hydrogen, cyano or $C_{1-4}$ alkyl, m is 0 or 1, $R^2$ is hydrogen, $C_{1-6}$ alkyl, $C_{3-4}$ alkenyl unsubstituted or substituted by halogen, $C_{3-4}$ alkynyl, $C_{3-8}$ cycloalkyl unsubstituted or substituted by methyl, unsubstituted phenyl or phenyl substituted by halogen, unsubstituted benzyl or benzyl substituted by halogen, hydroxy, $C_{1-4}$ alkoxy or —CH$_2$—Z, in which Z is as defined above, $R^3$ is —O—$R^4$, —S—$R^4$ or

in which $R^4$ is $C_{1-6}$ alkyl, $C_{3-4}$ alkenyl, $C_{3-4}$ alkynyl, $C_{3-8}$ cycloalkyl, unsubstituted phenyl or phenyl substituted by halogen, unsubstituted benzyl or benzyl substituted by halogen, or —(CH$_2$)$_n$—Z, in which n is 1 or 2 and Z has the same meaning as stated above, and $R^5$ and $R^6$ are hydrogen, $C_{1-9}$ alkyl unsubstituted or substituted by at least one substituent selected one substituent selected from the group consisting of halogen, hydroxy, mercapto, $C_{1-2}$ alkoxy, $C_{1-2}$ alkylthio, $C_{3-6}$ cycloalkyl, amino, $C_{1-2}$ monoalkylamino, $C_{2-4}$(in total) di-alkylamino, carboxy, $C_{1-2}$ alkoxy-carbonyl and cyano, unsubstituted $C_{3-4}$ alkenyl or $C_{3-4}$ alkenyl substituted by halogen, $C_{3-4}$ alkynyl, unsubstituted phenyl or phenyl substituted by halogen, unsubstituted benzyl or benzyl substituted by halogen, $C_{1-4}$ alkoxy, hydroxy, formyl, $C_{1-4}$ alkoxycarbonyl, $C_{1-4}$ alkylamino, $C_{2-4}$(in total)di-alkylamino, amino or

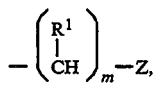

in which $R^1$, Z and m have the same meanings as stated above, and in addition, $R^5$ and $R^6$ may form, together with the N atom to which they are bonded, a pyrrolidino, piperidino, morpholino, piperazino or isoxazolidino ring which is unsubstituted or substituted by $C_{1-2}$ alkyl.

2. A cyano compound of the formula (I) according to claim 1, wherein $R^1$ is hydrogen or $C_{1-3}$ alkyl, m is 0 or 1

$R^2$ is hydrogen, $C_{1-4}$ alkyl, allyl, propargyl, phenyl unsubstituted or substituted by halogen, benzyl unsubstituted or substituted by halogen, hydroxy, or $C_{1-3}$ alkoxy, $R^3$ is —O—$R^4$, —S—$R^4$ or

in which $R^4$ is $C_{1-4}$ alkyl, allyl, propargyl, $C_{3-6}$ cycloalkyl, phenyl unsubstituted or substituted by halogen, or benzyl unsubstituted or substituted by halogen, $R^5$ and $R^6$ are hydrogen, $C_{1-9}$ alkyl unsubstituted or substituted by fluorine or chlorine, allyl unsubstituted or substituted by chlorine, propargyl, phenyl unsubstituted or substituted by chlorine, benzyl unsubstituted or substituted by chlorine, $C_{1-3}$ alkoxy, hydroxy, hydroxy-$C_{1-2}$ alkyl, mercapto-$C_{1-2}$ alkyl, amino-$C_{1-2}$ alkyl, $C_{1-3}$ alkylamino, dimethylamino, amino, cyano-$C_{1-2}$ alkyl, or —CH$_2$—$Z^2$ in which $Z^2$ is 5-thiazolyl unsubstituted or substituted by halogen, and in addition, $R^5$ and $R^6$ may form, together with the N-atom to which they are bonded, a pyrrolidino, piperidino, morpholino, piperazino or isoxazolidino ring which is unsubstituted or substituted by methyl.

3. A cyano compound of the formula (I) according to claim 1, wherein $R^1$ is hydrogen, methyl, ethyl or propyl, m is 0 or 1

$R_2$ is hydrogen, methyl, ethyl, propyl, allyl, propargyl, phenyl unsubstituted or substituted by chlorine, hydroxy, methoxy, or ethoxy, $R^3$ is —O—$R^4$, —S—$R^4$ or

in which $R^4$ is $C_{1-3}$ alkyl, allyl, propargyl cyclohexyl, phenyl, or benzyl unsubstituted or substituted by chlorine, $R^5$ and $R^6$ are hydrogen, $C_{1-4}$ alkyl unsubstituted or substituted by fluorine or chlorine, allyl unsubstituted or substituted by chlorine, propargyl, phenyl unsubstituted or substituted by chlorine, benzyl unsubstituted or substituted by chlorine, methoxy, hydroxy, hydroxyethyl, $C_{1-2}$ alkylamino, dimethylamino, amino, cyanoethyl, or 2-chloro-5-thiazolymethyl, and in addition, $R^5$ and $R^6$ may form, together with the N-atom to which they are bonded, pyrrolidino, piperidino, 2-methylpiperidino, morpholino, piperazino or isoxazolidino.

4. A compound according to claim 1, wherein such compound is

S-methyl-N-(2-chloro-5-thiazolylmethyl)-N'-cyanoisothioura of the following formula:

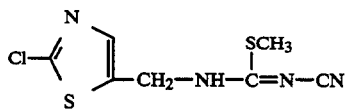

or

S-methyl-N-(2-chloro-5-thiazolylmethyl)-N'-cyanoisothiourea of the following formula:

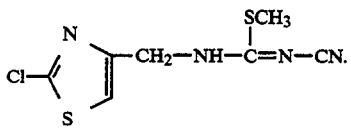

5. An insecticidal composition comprising an insecticidally effective amount of a cyano compound according to claim 1 in admixture with a diluent.

6. A method of combating insects which comprises applying to insects or to a habitat of insects an insecticidally effective amount of a cyano compound according to claim 1.

7. A method according to claim 6, wherein said cyano compound is

S-methyl-N-(2-chloro-5-thiazolylmethyl)-N'-cyanoisothiourea.

8. A compound according to claim 1, which has the formula:

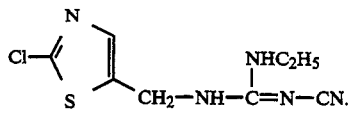

9. The method according to claim 6, wherein said cyano compound has the formula:

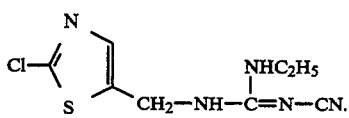

* * * * *

UNITED STATES PATENT AND TRADEMARK OFFICE
CERTIFICATE OF CORRECTION

PATENT NO.  : 5,384,324
DATED       : January 24, 1995
INVENTOR(S) : Shiokawa, et al.

It is certified that error appears in the above-indentified patent and that said Letters Patent is hereby corrected as shown below:

Title Page          [75] Inventors: After " Tsuboi " delete
                    " Hino " and substitute -- Tokyo --;
                    after " Honda, " delete " Tanashi " and
                    substitute -- Tokyo --; after " both of "
                    delete " Hachioji " and substitute
                    -- Tokyo --

Col. 41, line 4     Delete " thiazolymethyl " and substitute
                    -- thiazolylmethyl --

Signed and Sealed this

Seventh Day of October, 1997

Attest:

BRUCE LEHMAN

Attesting Officer    Commissioner of Patents and Trademarks